United States Patent [19]

Dékány et al.

[11] Patent Number: 4,782,141

[45] Date of Patent: Nov. 1, 1988

[54] PROCESS FOR PREPARING PRIMYCIN SALTS

[75] Inventors: Gyula Dékány; Judit Frank, both of Budapest, Hungary

[73] Assignee: Chinoin Gyogyszer ES Vegyeszeti Termekek Gyara RT., Budapest, Hungary

[21] Appl. No.: 751,624

[22] Filed: Jul. 2, 1985

[30] Foreign Application Priority Data

Jul. 3, 1984 [HU] Hungary ........................ 2571/84

[51] Int. Cl.$^4$ ............................................. C07H 15/04
[52] U.S. Cl. ........................................ 536/6.5; 536/122
[58] Field of Search ............... 536/6.5, 121, 17.1, 122; 514/31

[56] References Cited

U.S. PATENT DOCUMENTS

| ',518,135 | 8/1950 | Gaver ................... | 536/121 |
| 2,609,368 | 9/1952 | Gaver ................... | 536/121 |
| 3,244,590 | 4/1966 | Schaffner et al. ........ | 536/6.5 |
| 3,498,884 | 3/1970 | Valyi-Nagy et al. ...... | 435/76 |
| 4,035,568 | 7/1977 | Schaffner et al. ........ | 536/6.5 |
| 4,404,189 | 9/1983 | Kulsar et al. ........... | 424/114 |

FOREIGN PATENT DOCUMENTS

756856  3/1971 Belgium ................... 514/31
179148 12/1979 Hungary .

OTHER PUBLICATIONS

Merck Index, 10th Edition, Compound 7652.

*Primary Examiner*—J. R. Brown
*Assistant Examiner*—Elli Peselev
*Attorney, Agent, or Firm*—Herbert Dubno; Jonathan Myers

[57] ABSTRACT

This invention relates to salts of primycin formed with an organic acid—preferably a $C_{1-16}$ aliphatic carboxylic acid, a halogenated carboxylic acid, an aliphatic dicarboxylic acid, an aromatic carboxylic acid, a substituted aromatic carboxylic acid or an organic sulfonic acid—or an inorganic acid—preferably a hydrohalogenic acid.

There is furtheron provided a process for the preparation of new primycin salts which comprises reacting a suspension of primycin sulfate formed with an aliphatic alcohol containing 1-4 carbon atoms with a barium salt.

The new primycin salts of the present invention possess excellent antibiotic properties.

6 Claims, No Drawings

PROCESS FOR PREPARING PRIMYCIN SALTS

This invention relates to primycin salts, a process for the preparation thereof and pharmaceutical compositions comprising the same.

Primycin is a macrolide type antibiotic (Nature 174, 1105 (1954)). The preparation of primycin by culturing a Streptomyces primycini fungi strain and isolating thereof in the form of the sulfate salt is described in Hungarian Pat. No. 146 332. An improvement of the working-up procedure is disclosed in Hungarian patent of Addition No. 151 197. According to Hungarian Pat. No. 153 593 fermentation is carried out by using a Thermopolyspora galeriensis fungi strain. Hungarian patent No. 179 148 relates to a modification of the working-up procedure, wherein a process for the isolation of primycin sulfate, setting free the base by treatment of the sulfate with an alkali and preparation of salts formed with mineral acids other than sulfuric acid from the said base is set forth.

Recent detailed and sensitive thin layer chromatography (referred to furtheron as TLC) studies have shown however that alkaline treatment of primycin sulfate leads to a conversion of the fine structure of primycin and for this reason the fine structure of the salts prepared from the base thus obtained is no longer identical with that of the starting material.

It is the object of the present invention to provide primycin salts having an identical fine structure with that of primycin antibiotic.

It is a further object of the present invention to provide a new salt-formation process which enables the direct formation of various primycin salts from primycin sulfate readily available on industrial scale, whereby alkaline treatment of primycin sulfate is eliminated and consequently the original fine structure and antibiotic activity of primycin remains unchanged and unmodified in the course of the procedure.

The present invention is based on the recognition that by using barium salts various primycin salts can be directly obtained from primycin sulfate without the addition of an alkali. The barium sulfate formed can be easily removed from the reaction mixture by filtration and thus various primycin salts can be prepared by a very simple method in a highly pure form.

According to an aspect of the present invention there are provided salts or primycin formed with an organic acid—preferably a $C_{1-16}$ aliphatic carboxylic acid, a halogenated carboxylic acid, an aliphatic dicarboxylic acid, an aromatic carboxylic acid, a substituted aromatic carboxylic acid or an organic sulfonic acid—or an inorganic acid—preferably a hydrohalogenic acid.

Preferred representatives of the primycin salts according to the present invention are the following salts: Primycin formate, Primycin acetate, Primycin monochloro acetate, Primycin trichloro acetate, Primycin propionate, Primycin palmitate, Primycin oxalate, Primycin perchlorate, Primycin bromide, Primycin iodide, Primycin benzoate, Primycin mesylate, Primycin tosylate.

According to a further feature of the present invention there is provided a process for the preparation of new primycin salts which comprises reacting a suspension of primycin sulfate formed with an aliphatic alcohol containing 1-4 carbon atoms with a barium salt.

The barium salts may be prepared from barium carbonate or barium hydroxide with the aid of a suitable salt-forming reagent. As salt-forming reagent any organic or inorganic acid may be used which forms a barium salt soluble in water and/or an organic solvent (preferably in a $C_{1-4}$ alcohol). Thus the salt-forming reagent may be an organic acid, preferably a $C_{1-16}$ aliphatic carboxylic acid (e.g. formic acid, acetic acid, palmitic acid), a halogenated aliphatic carboxylic acid (e.g. trichloro acetic acid, monochloro acetic acid, etc.), an aliphatic dicarboxylic acid (e.g. oxalic acid), an aromatic carboxylic acid (e.g. benzoic acid), a substituted aromatic carboxylic acid (e.g. picrin acid), an aromatic sulfonic acid (e.g. p-toluene sulfonic acid, methane sulfonic acid), or an inorganic acid, e.g. a halogeno acid (e.g. a hydrogen halide such as hydrogen bromide, hydrogen iodide or perchloric acid). The barium salts may be in situ prepared by dissolving barium carbonate in the salt-forming reagent or dissolving barium carbonate in a $C_{1-4}$ alcohol—preferably methanol—and thereafter adding the salt-forming reagent, evaporating the solution thus obtained in vacuo and dissolving the residue in ether or a $C_{1-4}$ aliphatic alcohol, preferably methanol. According to another method the barium salts are prepared from barium hydroxide, within a saturated aqueous solution of barium hydroxide is reacted with a solution of the salt-forming reagent and a $C_{1-4}$ aliphatic alcohol—preferably ethanol—and/or water, whereafter the precipitated barium salt is removed by filtration from the system.

According to the process of the present invention one may proceed preferably by reacting a suspension of primycin sulfate and a $C_{1-4}$ aliphatic alcohol—preferably methanol—with the corresponding barium salt at a temperature between 20° C. and 80° C.—particularly at the boiling point of the solvent—and removing the precipitated barium sulfate by filtration. It is preferred to carry out the reaction at the boiling point of the reaction mixture which on the one hand makes the reaction complete and on the other enhances the precipitation of barium sulfate in a more readily soluble form. Thus the removal of barium sulfate is made easier. Barium sulfate may be removed by filtering the mixture hot, preferably through a suitable filtration auxiliary agent, particularly by using Celite. The filtrate is evaporated in vacuo and the residual solid is treated with ether, filtered, washed with ether and/or a 2:1 mixture of acetone and water and dried. The various primycin salts are obtained in the form of a powdery product.

The new primycin salts of the present invention show a better solubility than the hitherto known primycin sulfate and this results in an improvement of the absorption conditions.

The antibacterial activity of the new primycin salts of the present invention is tested on gram positive and gram negative bacteria and gemmiparous fungi; the test microorganisms are enumerated in Table I.

The tests show that the primycin salts exhibit an outstanding activity on gram positive bacteria while the effect on gram negative bacteria and gemmiparous fungi is lower.

In the tests a Difco-bouillon nutrient medium is used in the case of bacteria and a Sabouiraud nutrient medium is applied for fungi. Inoculation is carried out in a concentration of $5 \times 10^5 - 5 \times 10^6$ cells/ml, at a temperature of 37° C. for 24 hours. The minimal inhibitory concentration (MIC) values are determined by the series dilution method and expressed as µg/ml.

A stock solution having a concentration of 1000 µg/ml is prepared in a 1:1:2 mixture of butanol, ethanol and water. The said stock solution is diluted with water. The MIC values are summarized in Table II.

The following primycin salts are used:
I Primycin acetate
II Primycin formate
III Primycin propionate
IV Primycin trichloro acetate
V Primycin perchlorate
VI Primycin oxalate
VII Primycin palmitate
VIII Primycin tosylate
IX Primycin benzoate
X Primycin iodide
XI Primycin bromide.

TABLE I

The designation of the strains is as follows:

| | | |
|---|---|---|
| 1. | Staphylococcus aureus | CCM.885 |
| 2. | Staphylococcus aureus | DSM.20231 |
| 3. | Staphylococcus aureus | CCM.2317 |
| 4. | Staphylococcus aureus | CCM.2326 |
| 5. | Staphylococcus aureus | CCM.2514 |
| 6. | Staphylococcus aureus | CCM.2515 |
| 7. | Staphylococcus epidermidis | CCM.2271 |
| 8. | Staphylococcus aureus Smith | |
| 9. | Streptococcus faecalis | CCM.1875 |
| 10. | Streptococcus agalactiae | CCM.5153 |
| 11. | Streptococcus agalactiae | CCM.5534 |
| 12. | Streptococcus disgalactiae | CCM.5548 |
| 13. | Bacillus subtilis | ATCC.6633 |
| 14. | Bacillus cereus | CCM.2010 |
| 15. | Bacillus licheniformis | CCM.2182 |
| 16. | Bacillus licheniformis | CCM.2205 |
| 17. | Bacillus subtilis | CCM.1718 |
| 18. | Listeria monocytogenes | CCM.5576 |
| 19. | Micrococcus flavus | ATCC.10240 |
| 20. | Micrococcus luteus | DSM.20030 |
| 21. | Sporosarcina ureae | DSM.317 |
| 22. | Pseudomonas aeruginosa | CCM.1960 |
| 23. | Proteus vulgaris | CCM.1799 |
| 24. | Shigella sonnei | CCM.1373 |
| 25. | Salmonella typhimurium | CCM.5445 |
| 26. | Saccharomyces cerevisiae | OKI.1282 |
| 27. | Candida albicans | CBS.562 |

TABLE I-continued

The designation of the strains is as follows:

| | | |
|---|---|---|
| 28. | Candida tropicalis | CBS.433 |

TABLE II

Activity spectrum of primycin salts on polyresistant bacteria and gemmiparous fungi

| Tested microorg. | Primycin-Salts | | | | | | | | | | |
|---|---|---|---|---|---|---|---|---|---|---|---|
| | I | II | III | IV | V | VI | VII | VIII | IX | X | XI |
| 1 | 0.25 | 0.1 | 0.1 | 0.1 | 0.1 | 0.05 | 0.05 | 0.25 | 0.25 | 0.075 | 0.075 |
| 2 | 0.075 | 0.05 | 0.075 | 0.05 | 0.075 | 0.05 | 0.05 | 0.1 | 0.25 | 0.075 | 0.075 |
| 3 | 0.075 | 0.075 | 0.075 | 0.05 | 0.075 | 0.05 | 0.05 | 0.1 | 0.25 | 0.075 | 0.075 |
| 4 | 0.25 | 0.1 | 0.25 | 0.075 | 0.1 | 0.05 | 0.05 | 0.25 | 0.25 | 0.075 | 0.075 |
| 5 | | 0.075 | 0.05 | 0.05 | 0.05 | 0.025 | 0.025 | 0.1 | 0.25 | 0.05 | 0.05 |
| 6 | | 0.05 | 0.025 | 0.05 | 0.025 | 0.025 | 0.01 | 0.05 | 0.25 | 0.05 | 0.05 |
| 7 | | 0.1 | 0.075 | 0.05 | 0.05 | 0.025 | 0.025 | 0.075 | 0.25 | 0.075 | 0.075 |
| 8 | | 0.075 | 0.075 | 0.075 | 0.05 | 0.05 | 0.05 | 0.25 | 0.25 | 0.05 | 0.075 |
| 9 | 2.5 | 2.5 | 5 | 2.5 | 2.5 | 1 | 10 | 2.5 | 5 | 2.5 | 5 |
| 10 | | 0.075 | 0.5 | 0.25 | 0.1 | 0.075 | 0.075 | 0.25 | 0.25 | 0.25 | 0.25 |
| 11 | 0.5 | 0.5 | 0.5 | 0.5 | 0.5 | 0.1 | 0.25 | 0.75 | 0.75 | 0.5 | 0.5 |
| 12 | 1 | 0.75 | 0.75 | 0.75 | 1 | 0.5 | 0.75 | 1 | 1 | 0.75 | 0.75 |
| 13 | 0.05 | 0.05 | 0.05 | 0.075 | 0.075 | 0.025 | 0.025 | 0.075 | 0.25 | 0.075 | 0.075 |
| 14 | 0.25 | 0.05 | 0.1 | 0.075 | 0.075 | 0.05 | 0.05 | 0.1 | 0.25 | 0.075 | 0.05 |
| 15 | | 0.075 | 0.075 | 0.075 | 0.075 | 0.05 | 0.075 | 0.1 | 0.25 | 0.075 | 0.075 |
| 16 | | 0.05 | 0.05 | 0.075 | 0.05 | 0.05 | 0.05 | 0.075 | 0.25 | 0.05 | 0.05 |
| 17 | | 0.05 | 0.05 | 0.05 | 0.05 | 0.05 | 0.05 | 0.05 | 0.25 | 0.05 | 0.025 |
| 18 | | 0.25 | 0.25 | 0.25 | 0.25 | 0.1 | 0.25 | 0.25 | 0.25 | 0.5 | 0.25 |
| 19 | | 0.025 | 0.025 | 0.025 | 0.05 | 0.025 | 0.025 | 0.05 | 0.25 | 0.025 | 0.025 |
| 20 | | 0.025 | 0.025 | 0.025 | 0.025 | 0.025 | 0.05 | 0.05 | 0.5 | 0.025 | 0.05 |
| 21 | | 0.025 | 0.01 | 0.01 | 0.025 | 0.025 | 0.1 | 0.025 | 0.5 | 0.01 | 0.01 |
| 22 | 25 | 25 | 25 | 25 | 25 | 25 | 25 | 25 | 25 | 25 | 25 |
| 23 | 25 | 25 | 10 | 25 | 25 | 25 | 25 | 25 | 25 | 25 | 25 |
| 24 | 50 | 25 | 10 | 25 | 25 | 25 | 25 | 25 | 25 | 25 | 25 |
| 25 | 50 | 25 | 25 | 25 | 25 | 25 | 25 | 25 | 25 | 25 | 25 |
| 26 | 50 | 25 | 25 | 25 | 25 | 25 | 25 | 25 | 25 | 10 | 50 |
| 27 | 25 | 25 | 25 | 10 | 10 | 10 | 25 | 25 | 25 | 25 | 25 |
| 28 | 50 | 25 | 25 | 10 | 25 | 25 | 25 | 25 | 25 | 10 | 25 |

According to a still further aspect of the present invention there are provided pharmaceutical compositions having antibiotic effect comprosing as active ingredient a salt of primycin formed with an inorganic or organic acid—other than the salt formed with sulfuric acid—and optionally one or more other antimicrobial compound in admixture with suitable inert pharmaceutical carriers, fillers and/or auxiliary agents.

The primycin salts of the present invention may be finished in solid (e.g. tablets, capsules, coated pills, dragées, suppositories), semisolid (e.g. ointment, jelly) or liquid (e.g. injectable solution, suspension or syrup) form. Preferred dosage forms are the jellies, wound dusting powders, injectable solutions or suspensions and combinations powder ampouls and solvent ampouls.

The pharmaceutical compositions of the present invention are suitable for oral, parenteral or rectal administration or for local use (e.g. ointments). The said pharmaceutical compositions may comprise usual and conventional pharmaceutical carriers (e.g. magnesium carbonate, magnesium stearate, starch, talc, water, etc.), or as further active ingredient cyclodextrin and optionally auxiliary agents (e.g. disintegrating agents, emulsifying agents, etc.).

The compositions suitable for oral administration may be preferably tablets, capsules, coated pills or dragées. The compositions comprising primycin salts may be used in veterinary therapy as well, e.g. as solution to be introduced into the fodder. The parenteral compositions may be aqueous emulsions, solutions or suspensions. Compositions for local application may be dusting powders, ointments, aqueous or oily emulsions or bandages or dressing material impregnated with such solutions, or suspensions or sprays.

According to a still further feature of the present invention there is provided a process for the preparation of pharmaceutical compositions which comprises admixing a salt of primycin formed with an organic or inorganic acid—other than the salt formed with sulfuric acid—and optionally a further antimicrobial agent as active ingredient with suitable inert pharmaceutical carriers, fillers and/or auxiliary agents.

Further details of the present invention are to be found in the following Examples of non-limiting character. The solvent mixtures used in the Examples are expressed in volume/volume ratio unless otherwise stated.

EXAMPLE 1

0.088 g (0.446 millimole) of barium carbonate are heated to boiling in 5 ml of formic acid until a clear solution is obtained. The colorless solution is evaporated to dryness in vacuo. The residue is dissolved in 10 ml of methanol and the solution thus obtained is added to a suspension of 1.0 g (0.887 millimole) or primycin sulfate and 70 ml of methanol. The reaction mixture is heated to boiling for 10 minutes under constant stirring. The precipitated barium sulfate is filtered hot through a Celite filtration auxiliary agent. The filtrate is evaporated in vacuo and the solid residue is treated with ether. The white powdery product is washed with 20 ml of a 2:1 mixture of acetone and water and thereafter with anhydrous ether. Thus 0.96 g of primycin formate is obtained, yield 94.8%. Mp.: 162°–164° C., $/\alpha/_D^{25} = +31.9°$. (in a 2:2:1 mixture of n-butanol, ethanol and water, c=0.1%)

EXAMPLE 2

0.88 g (4.459 millimoles) of anhydrous barium carbonate is stirred in 10 ml of acetic acid at 100° C. until the solid goes completely into solution. The solvent is removed in vacuo. The residue is dissolved in 20 ml of methanol, and the solution is poured into a suspension of 10 g (8.87 millimoles) of primycin sulfate in 600 ml of methanol. The suspension is heated to boiling for 10 minutes under constant stirring. The precipitated barium sulfate is filtered off through a Celite filtration auxiliary agent and the filtrate is evaporated in vacuo. The residue is treated with 50 ml of a 2:1 mixture of acetone and water and filtered. The solid is dried under an infra lamp. Thus 9.4 g of primycin acetate are obtained, yield 91.43%. Mp.: 186°–188° C., $/\alpha/_D^{25} = +30°$.

EXAMPLE 3

0.088 g (0.446 millimoles) of anhydrous barium carbonate and 0.146 g (0.887 millimoles) of trichloro acetic acid are heated in 20 ml of methanol until all the barium carbonate is dissolved. The hot and colorless solution is added to a suspension of 1.0 g (0.088 millimoles) of primycin sulfate and 80 ml of methanol. The reaction mixture is heated to boiling for 20 minutes. The precipitated barium sulfate is filtered hot and the filtrate is evaporated in vacuo. The solid residue is treated with ether, dried and the powdery product is washed with 15 ml of a 2:1 mixture of acetone and water. Thus 0.96 g of primycin trichloro acetate are obtained, yield 85.9%. Mp.: 165°–166° C., $/\alpha/_D^{25} = +17.7°$.

EXAMPLE 4

0.088 g (0.446 millimoles) of barium carbonate are stirred in 15 ml propionic acid at 100° C. until all the barium carbonate is dissolved. The colorless solution is evaporated in vacuo. The residue is dissolved in 10 ml of methanol whereupon the solution is poured into a suspension of 1.0 g (0.887 millimoles) of primycin sulfate and 60 ml of methanol. The suspension is heated to boiling for 10 minutes under constant stirring. The precipitated barium sulfate is filtered hot over a Celite filtration auxiliary agent. The filtrate is evaporated in vacuo. The residue is treated with 20 ml of a 2:1 mixture of acetone and water and filtered. Thus 0.95 g of beige colored primycin propionate is obtained, yield 91.3%. Mp.: 170° C., $/\alpha/_D^{25} = +36.9°$.

EXAMPLE 5

0.22 g (0.887 millimoles) of palmitic acid are dissolved in 15 ml of methanol and so much water is added dropwise to the solution that the palmitic acid should not precipitate. To the solution thus obtained 2.51 ml of a saturated barium hydroxide solution are added. The precipitated barium salt is filtered and added to a suspension of 1.0 g (0.887 millimoles) of primycin sulfate and 120 ml of methanol. The reaction mixture is heated to boiling for an hour whereby the barium palmitate is dissolved and the insoluble barium sulfate is precipitated. The hot reaction mixtures is filtered over Celite. The filtrate is evaporated in vacuo. The residue is treated with ether and filtered again. The solid is washed on the filter with a 2:1 mixture of acetone and water and dried until constant weight. Thus 0.98 g of primycin palmitate are obtained, yield 82.2%. Mp.: 180°–181° C., $/\alpha/_D^{25} = +30$.

EXAMPLE 6

0.087 g (0.444 millimoles) of barium carbonate are suspended in 15 ml of mthanol whereupon 0.04 g (0.444 millimoles) of oxalic acid are added. The suspension thus obtained is heated to boiling until all the solid is dissolved (about 10 minutes). The solvent is removed in vacuo. The residue is added to a solution of 1.0 g (0.887 millimoles) of primycin sulfate and 80 ml of methanol and the reaction mixture is heated to boiling for 20 minutes under constant stirring. The precipitated barium sulfate is filtered hot over Celite. The filtrate is evaporated in vacuo. The solid residue is treated with ether and filtered. The solid is washed on the filter with a 2:1 mixture of acetone and water. Thus 0.93 g of white primycin oxalate is obtained, yield 92.2%. Mp.: 186°–187° C., $/\alpha/_D^{25} = +40°$.

EXAMPLE 7

0.087 g (0.444 millimoles) of barium carbonate is dissolved in 8.87 ml of a 0.1N aqueous perchloric acid solution under slight warming whereupon water is removed in vacuo. The residue is taken up in 10 ml of methanol and added to a suspension of 1.0 g (0.887 millimoles) of primycin sulfate in 80 ml of methanol. The reaction mixture is heated to boiling for 20 minutes under stirring. The primycin perchlorate thus formed remains in the solution and the barium sulfate is precipitated. The hot solution is filtered over Celite and the solid is thoroughly washed on the filter with 10 ml of a 2:1 mixture of acetone and water. Thus 0.94 g of white primycin perchlorate is obtained, yield 88.7%. Mp.: 170°–171° C., $/\alpha/_D^{25} = +20°$.

EXAMPLE 8

0.087 g (0.444 millimoles) of barium carbonate is dissolved in 1 ml of 48% hydrogen bromide under slight warming. The solvent is removed in vacuo and the residue is rubbed with ether. The barium bromide is filtered and washed with dichloro methane until all the traces of bromine are removed. The yellow color of barium bromide turns into light beige. This salt is dissolved in 10 ml of methanol and the solution is added to a solution of 1.0 g (0.887 millimoles) of primycin sulfate and 80 ml of methanol. The suspension thus obtained is heated to boiling for 20 minutes under stirring. The precipitated barium sulfate is filtered and the filtrate is evaporated in vacuo. The residue is treated with ether and filtered. The solid is washed on the filter first with 10 ml of a 2:1 mixture of acetone and water and later with 10 ml of a dichloro methane. Thus 0.91 g of beige primycin bromide is obtained, yield 87.2%. Mp.: 138° C., $/\alpha/_D^{25} = -20°$.

EXAMPLE 9

0.087 g (0.444 millimoles) of barium carbonate is dissolved in 1.5 ml of 57% methanolic hydrogen iodide under slight warming. The solvent is removed in vacuo. The residue is trated with ether and thoroughly washed with 30 ml of dichloro methane. The yellow barium iodide thus obtained is dissolved in 15 ml of methanol whereupon the solution is added to a suspension of 1.0 g (0.887 millimoles) of primycin sulfate and 80 ml of methanol. In order to bring the primycin iodide formed completely into solution, the suspension is heated to boiling for 20 minutes under stirring. The hot reaction mixture is dried and filtered through Celite. The filtrate is evaporated in vacuo. The residue is treated with ether and filtered. The product is washed on the filter iodine-free with 10 ml of a 2:1 mixture of acetone and water and thereafter with dichloro methane. Thus 0.93 g of yellow primycin iodide are obtained, yield 85.7% Mp.: 178° C., $/\alpha/_D^{25} = +10°$.

EXAMPLE 10

0.087 g (0.444 millimole) of barium carbonate are suspended in 15 ml of methanol whereupon 0.11 g (0.91 millimole) of benzoic acid is added. The suspension thus obtained is heated to boiling until a clear solution is obtained. The clear and colorless solution is added to a suspension of 1.0 g (0.887 millimoles) of primycin sulfate and 80 ml of methanol and the reaction mixture is heated to boiling for 20 minutes under stirring. The hot solution is filtered through Celite and the filtrate is evaporated to dryness in vacuo. The residue is treated with ether, filtered and the solid is washed on the filter with 15 ml of a 2:1 mixture of acetone and water. Thus 0.98 g of primycin sulfate is obtained in the form of a white powder, yield 90.6%. Mp.: 170°–171° C., $/\alpha/_D^{25} = +36.9°$.

EXAMPLE 11

0.088 g (0.446 millimoles) of barium carbonate and 0.169 g (0.892 millimoles) of p-toluene sulfonic acid monohydrate are heated to boiling in 20 ml of methanol until all the substance goes into solution. The colorless hot solution thus obtained is poured into a suspension of 0.1 g (0.887 millimoles) of primycin sulfate and 80 ml of methanol. The reaction mixture is heated to boiling for 15 minutes under constant stirring. The hot mixture is filtered through Celite. The filtrate is evaporated in vacuo. The residue is suspended in a 2:1 mixture of acetone and water, filtered and washed with the above solvent mixture. Thus 1.05 g of white primycin tosylate are obtained, yield 93.3%. The salt decomposes on heating, $/\alpha/_D^{25} = -3.9°$.

EXAMPLE 12

0.088 g (0.446 millimoles) of barium carbonate and 0.21 g (2.23 millimoles) of monochloro acetic acid are dissolved in 10 ml of a 1:1 mixture of methanol and water under heating. The still hot solution is added to a suspension of 1.0 g (0.887 millimoles) of primycin sulfate and 70 ml of methanol. The reaction mixture is heated to boiling for 10 minutes under constant stirring, the precipitated barium sulfate is filtered through Celite. The filtrate is evaporated in vacuo. The solid residue is treated with ether. The white powdery solid is washed on the filter three times with 10 ml of ether saturated with water each and dried to constant weight. Thus 0.97 g of primycin monochloroacetate is obtained, yield 93.3%. Mp.: 176° C., $/\alpha/_D^{25} = +22.0°$.

In the following Examples the preparation of characteristic formulations comprising as active ingredient a primycin salt according to the present invention is described.

EXAMPLE 13

Preparation of dusting powder

| Component | Amount, g |
|---|---|
| Primycin salt | 1.0 |
| Cyclodextrin | 9.0 |
| Total weight | 10.0 |

EXAMPLE 14

Preparation of dusting powder

| Component | Amount, g |
|---|---|
| Primycin salt | 1.0 |
| Amylum non mucilaginosum | 9.0 |
| Total weight | 10.0 |

EXAMPLE 15

Preparation of dusting powder

| Component | Amount, g |
|---|---|
| Primycin salt | 1.0 |
| *Aetheroleum lavandulae* | 0.02 |
| Colloidal silicic acid | 0.10 |
| Magnesium stearate | 0.10 |
| Zinc oxide | 0.20 |
| Bolus alba | 0.50 |
| Magnesium carbonicum hydroxidatum | 1.00 |
| B-cyclodextrin | 7.08 |
| Total weight | 10.00 |

EXAMPLE 16

Preparation of aerosol

| Component | Amount, g |
|---|---|
| Primycin salt | 0.20 |
| Isopropyl myristate | 1.00 |
| Freon 11/12 5050 (carrier gas) | 98.80 |
| Total weight | 100.00 |

EXAMPLE 17

Preparation of aqueous aerosol

| Component | Amount, g |
|---|---|
| Primycin salt | 0.5 g |
| ethanol (62.5 vol. %) | 10.0 |
| water | 39.5 |
| carrier gas | 50.0 |
| Total weight | 100.0 |

EXAMPLE 18

Preparation of an aerosol wound dressing

| Component | Amount, g |
|---|---|
| Primycin salt | 0.1 |
| polyvinyl pyrrolidone | 1.50 |
| ethanol (62.5 vol. %) | 48.40 |
| carrier gas | 50.00 |
| Total weight | 100.00 |

EXAMPLE 19

Preparation of a jelly

| Component | Amount, g |
|---|---|
| primycin salt | 0.02 |
| chlorophyll | 0.002 |
| menthol | 0.2 |
| polyadipic acid | 0.12 |
| triethanol amine | 0.15 |
| Tween 20 | 0.15 |
| diisopropyl adipate | 0.50 |
| ethanol (96%) | 5.0 |
| distilled water, ad | 10.0 |

The above mixture is filled into flacons.

EXAMPLE 20

Preparation of a jelly

| Component | Amount, g |
|---|---|
| primycin salt | 0.20 |
| lidocaine | 2.00 |
| chlorophyll | 0.005 |
| menthol | 0.20 |
| Carbopol 940 | 1.20 |
| triethanol amine | 1.50 |
| Tween 20 | 1.50 |
| isoadipate | 5.00 |
| ethanol (96%) | 50.00 |
| distilled water, ad | 100.00 |

The above mixture is filled into flacons.

EXAMPLE 21

Preparation of an ointment

| Component | Amount, g |
|---|---|
| primycin salt | 2.00 |
| oleum paraffini | 33.00 |
| vasilinum album | 31.00 |
| ethanol (96%) | 20.00 |
| Tween 60 | 9.00 |
| cotton oil | 5.0 |

| Component | Amount, g |
|---|---|
| Total weight | 100.00 |

The above mixture is filled into a flacon or a crucible

EXAMPLE 22

Preparation of an eye ointment

| Component | Amount, g |
|---|---|
| primycin salt | 0.04 |
| ethanol (62.5 vol. %) | 0.08 |
| distilled water | 3.16 |
| Bee wachs | 300.00 |
| Cholesterol | 25.00 |

The above mixture is diluted with sterile castor oil to 1000.0 g.

EXAMPLE 23

Ointment washable with water

| Component | Amount, g |
|---|---|
| primycin salt | 2.0 |
| Tween 60 | 5.0 |
| liquid paraffine | 5.0 |
| cetyl stearyl alcohol | 15.0 |
| white petroleum jelly | 25.0 |

The mixture is diluted with distilled water to 100.0 g.

EXAMPLE 24

Ointment washable with water

| Component | Amount, g |
|---|---|
| primycin salt | 0.100 g |
| ethanol (62.5 vol. %) | 2.000 g |
| water | 7.900 g |
| sorboxaethen stearate | 3.600 g |
| liquid praffine | 3.600 g |
| cetyl stearyl alcohol | 10.800 g |
| white petroleum jelly | 18.000 g |
| propyl-p-hydroxy-benzoate | 0.054 g |
| methyl-p-hydroxy-benzoate | 0.126 g |
| ethanol (96% vol. %) | 2.930 g |
| lidocaine chloride | 1.000 |

The mixture is diluted with distilled water to 100.0 g.

EXAMPLE 25

Preparation of eye drops

| Component | Amount, g |
|---|---|
| primycin salt | 0.02 |
| sodium bicarbonate | 18.00 |
| viscous solvent (4 g of methyl cellulose and 3.5 g of sodium chloride in 510 g of distilled water) | 510.00 |
| phenyl mercury borate (0.1%) | 15.10 |

The above mixture is diluted with distilled water to 1000.0 g.

EXAMPLE 26

Preparation of oily eye drops

| Component | Amount, g |
|---|---|
| primycin salt | 0.02 |
| ethanol (62.5 vol. %) | 0.40 |
| distilled water | 1.58 |
| cholesterol | 25.00 |

The above mixture is diluted with sterile castor oil to 100.0 g.

EXAMPLE 27

Preparation of vaginal suppositories

| Component | Amount, g |
|---|---|
| primycin salt | 0.02 |
| ethanol (62.5 vol. %) | 0.262 |
| gelatine | 1.40 |
| sodium acetate | 0.26 |
| glycerol | 4.50 |

The mixture is diluted with water to 9.5 g.

EXAMPLE 28

Preparation of soluble tablets

| Component | Amount, g |
|---|---|
| primycin salt | 0.4 |
| urea or sodium chloride | 9.6 |

The primycin salt and the filler are dissolved in 60% ethanol, the solvent is evaporated and the granulates are compressed into tablets.

EXAMPLE 29

Preparation of antimicrobial bandage

The primycin salt is dissolved in ethanol and the bandage (e.g. wound-dressing, mull) is impregnated with the solution thus obtained. The thus treated bandage is packed and sterilized in a known manner. The sterile bandage having antimicrobal effect thus obtained is suitable for use for any purposes.

What we claim is:

1. A process for the preparation of a salt of primycin formed with a pharmaceutically acceptable organic acid or inorganic halogenic acid, which comprises the steps of:
   (a) reacting a suspension of primycin sulfate in an aliphatic alcohol having 1 to 4 carbon atoms with a barium salt of the pharmaceutically acceptable organic acid or inorganic halogenic acid to produce a barium sulfate precipitate and a solution of the salt of primycin formed with a pharmaceutically acceptable organic acid or inorganic halogenic acid;
   (b) filtering the product of step (a) to remove the barium sulfate precipitate leaving behind a filtrate containing the salt of primycin formed with a pharmaceutically acceptable organic acid or inorganic halogenic acid; and
   (c) evaporating the filtrate to isolate the salt of primycin as a solid residue.

2. The process defined in claim 1 wherein the barium salt of the pharmaceutically acceptable organic acid or inorganic halogenic acid is formed in situ.

3. The process defined in claim 1 wherein the barium salt of the pharmaceutically acceptable organic acid or inorganic halogenic acid is prepared in situ by dissolving barium carbonate or a solution thereof formed with a $C_1$ to $C_4$ aliphatic alcohol in the pharmaceutically acceptable organic or inorganic halogenic acid, evaporating the solution thus obtained, and dissolving the residue in a $C_1$ to $C_4$ aliphatic alcohol or ether.

4. The process defined in claim 1 wherein the barium salt of the pharmaceutically acceptable organic or inorganic halogenic acid is prepared by reacting a saturated aqueous solution of barium hydroxide with a solution of the pharmaceutically acceptable organic acid or halogenic inorganic acid formed with a $C_1$ to $C_4$ aliphatic alcohol, water, or a combination thereof, and thereafter filtering the mixture.

5. The process defined in claim 1 wherein the reaction in step (a) is carried out at a temperature of 20° to 80° C.

6. The process defined in claim 1 wherein following step (c) the primycin salt solid residue is treated with a solvent.

* * * * *